United States Patent [19]

Hedlund et al.

[11] Patent Number: 5,416,078
[45] Date of Patent: May 16, 1995

[54] FLUID RESUSCITATION

[75] Inventors: Bo E. Hedlund, New Brighton; Philip E. Hallaway, Minneapolis, both of Minn.

[73] Assignee: Biomedical Frontiers, Inc., Minneapolis, Minn.

[21] Appl. No.: 949,522

[22] PCT Filed: Mar. 30, 1990

[86] PCT No.: PCT/US90/01768
§ 371 Date: Nov. 25, 1992
§ 102(e) Date: Nov. 25, 1992

[87] PCT Pub. No.: WO91/15215
PCT Pub. Date: Oct. 17, 1991

[51] Int. Cl.⁶ ............... A61K 31/715; A61K 31/185
[52] U.S. Cl. .................... 514/58; 514/54; 514/575; 514/832; 514/833; 514/836; 514/970; 562/874
[58] Field of Search ............ 514/58, 54, 575, 836, 514/970, 832, 833; 562/874

[56] References Cited

U.S. PATENT DOCUMENTS

| | | | |
|---|---|---|---|
| 4,684,482 | 8/1987 | Green | 564/153 |
| 4,863,964 | 9/1989 | Hedlund et al. | 514/575 |
| 4,900,780 | 2/1990 | Cerny | 514/6 |
| 4,994,444 | 2/1991 | Zikria | 514/60 |
| 5,248,507 | 9/1993 | e Silva et al. | 514/59 |

OTHER PUBLICATIONS

K. Rosenlof, "Beneficial Effects of Erythropoetin on Hematological Parameters Aerobic Capacity and Body Fluid Composition in Patients on Hemodialysis", Stn. File Service, BA89:41083', vol. 226, No. 5, 1989 pp. 311–318.

Lesnefsky et al., "Reactive Oxygen Metabolites, Myocardial Ischemia", Clinical Research Abstract, Feb. 5, 1990.

*Primary Examiner*—Ronald W. Griffin
*Attorney, Agent, or Firm*—Larson and Taylor

[57] ABSTRACT

The invention relates to fluid resuscitation of the human or animal body by administration of deferoxamine (DFO) and a water-soluble biopolymer.

The DFO and the biopolymer are preferably bonded together.

The biopolymer may be a polysaccharide or a protein.

The DFO and the biopolymer are preferably formulated as an aqueous solution suitable for oral administration.

The fluid resuscitation may be effected for ameliorating systemic oxidant injury occurring during ischemia and subsequent reperfusion.

The fluid resuscitation may be indicated in treatment of burn injury, lung injury caused by inhalation of hot and/or toxic substances, such as smoke derived from combustion, hemorrhagic shock and other types of trauma.

14 Claims, No Drawings

FLUID RESUSCITATION

FIELD OF THE INVENTION

The present invention relates to fluid resuscitation. Such resuscitation is required or is desirable in treatment of burn injury, lung injury caused by inhalation of hot and/or toxic substances, such as smoke derived from combustion, and hemorrhagic shock.

BACKGROUND OF THE INVENTION

Thermal injury and severe bleeding lead to shock. The acute therapeutic intervention is similar in both situations: primary treatment is fluid therapy. In the case of hemorrhagic shock, the lost blood volume must be replaced as quickly as possible. Initially lost blood volume is provided either by salt solutions, so called crystalloids, or with colloids, such as dextran or hydroxyethyl starch. If blood is available, the physician will replace lost blood by transfusion.

Burn injury is often accompanied by injury to the lungs caused by inhalation of hot and/or toxic substances, such as smoke, derived from combustion.

Severe burn injury affecting more than 15–20% of the total body area leads to tremendous loss of fluid through the burned skin and fluid replacement is an extremely important form of therapy for these patients. Both crystalloids and colloids are routinely used. Lung injury caused by smoke inhalation and other toxic fumes is also treated with fluids since the injury to the lung also causes loss of fluid.

The critical period of initial resuscitation, i.e. when fluid is administered, is the time when reperfusion injury occurs. During this period, which may be as short as a minute or as long as several hours, oxygen radical mediated injury appears to occur. Presently used volume expanders (crystalloids and colloids) do not provide the anti-oxidant properties necessary to mitigate such injury.

Deferoxamine (or desferrioxamine) and its pharmaceutically-acceptable salts are chelating agents. Deferoxamine mesylate is commercially available and is used to treat severe iron intoxication, iron storage disease or iron overload resulting from hemolysis due to drugs, thalassemia, sickle-cell anemia, frequent blood transfusions and the like.

There are a number of problems with the clinical use of deferoxamine mesylate. Since the drug is not appreciably absorbed when orally administered, it generally must be given parenterally. Once administered, the drug is very rapidly excreted. For example, in humans the drug is very rapidly excreted. For example, min. Chelation therapy with the drug, as a result, involves continuous infusion or frequent intramuscular injections, which may cause pain and/or induration at the injection site. Further, the acute and chronic toxicities of deferoxamine are relatively high, making the substance less versatile for therapeutic uses.

The substance deferoxamine is often abbreviated DFO or DES (not to be confused with diethylstilbesterol). For consistency, only the abbreviation DFO will be used herein. Terms such as "Dextran-DFO" mean an adduct of the polymer (dextran) with DFO. Such an adduct may include more than one DFO moiety per unit substrate.

EP-0 304 183A (corresponding to U.S. Pat. No. 4,863,964) discloses pharmaceutically acceptable water-soluble biopolymers covalently bonded to deferoxamine. Such biopolymers covalently bonded to deferoxamine are herein refused to as conjugates. Preferred conjugates consist of pharmaceutically acceptable water-soluble polysaccharides covalently bonded to deferoxamine, pharmaceutically acceptable water-soluble proteins covalently bonded to deferoxamine and water-soluble inulin-deferoxamine adducts.

It has now been discovered that such conjugates of deferoxamine are useful in fluid resuscitation.

It has also been discovered that DFO and water-soluble biopolymers even if not covalently bonded together may be useful in fluid resuscitation.

SUMMARY OF THE INVENTION

The present invention relates to the use of a pharmaceutically acceptable water-soluble biopolymer and deferoxamine (DFO) for use in fluid resuscitation.

In particular the invention relates to the use of such biopolymer and DFO for the preparation or manufacture of a medicament for use in fluid resuscitation.

The biopolymer may be covalently bonded to the DFO. Conjugation of DFO as described above decreases the toxicity of the DFO whilst not reducing or not proportionally reducing its chelating ability.

However, we have some indications that in certain circumstances, free DFO is not as toxic as commonly asserted.

Accordingly, it is within the scope of the invention to use the DFO and the biopolymer in combination with each other as described above but not covalently bound or otherwise conjugated together.

The biopolymer may be a polysaccharide or a protein.

Where the biopolymer is a polysaccharide, the DFO may be covalently bonded directly to aldehydde groups on the polysaccharide.

Where the biopolymer is a protein, the DFO may be covalently bonded directly to one or more amino, carbonyl or thiol groups on the protein.

The polysaccharide may comprise dextran, hyaulronic acid, inulin, starch, e.g. hydroxyethyl starch or other modified form of starch.

The protein may comprise serum albumin or other plasma protein fraction (human or animal) or hemoglobin.

It is evisaged that hemoglobin may be used in resuscitation fluids. Such fluids will provide oxygen to ischemic tissue but may be toxic due to release of iron from the iron-containing protein. The presence of DFO, either bound to or mixed with the hemoglobin may decrease such toxicity.

The DFO-conjugate may be prepared by method as described in EP-E-0 304 183A.

DFO and the biopolymer, whether or not conjugated together, are preferably formulated as an aqueous solution suitable for parenteral e.g. by intramuscular, intraperitoneal or intravenous infusion.

The conjugates between, and the simple mixtures of, polysaccharides and DFO preferably contain from 5 to 25% chelator by weight. It is preferred that solutions having conjugate concentrations between 2 and 10% (w/v), dissolved in saline or lactated Ringer's solution, are used for fluid resuscitation. Effective doses are generally in the range of from approximately 20 to 300 mg chelator/kg body weight, although higher doses of conjugated DFO can be given in certain circumstances, for example in the treatment of acute iron poisoning.

Care should be taken when administering the chelator in a form not conjugated to the colloid, since adverse reactions can occur even at moderate doses.

Fluid resuscitation using the biopolymer and the DFO ameliorates systemic oxidant injury occurring during ischemic and subsequent reperfusion.

The fluid resuscitation may be indicated in treatment of burn injury, lung injury caused by inhalation of hot and/or toxic substances, such as smoke, derived from combustion, hemorrhagic shock and other types of trauma.

Oxygen derived radicals, such as the hydroxyl radical, are cytotoxic and highly reactive molecules are thought to contribute to cellular death in hemorrhagic and thermal shock. Production of hydroxyl radical is catalyzed by transition metal ions. Chelation of transition metal ions with DFO prevents formation of hydroxyl radicals.

By using the DFO and biopolymer according to the present invention two goals are achieved. Firstly critical volume is provided and, secondly reperfusion injury is prevented or at least attenuated, by removing the iron that catalyzes the reactions leading to formation of oxygen and lipid radicals. This represents a major advance for treating shock and trauma, at the site of an accident, during transport to, and in the hospital.

The need for volume replacement following major thermal injury is less acute than in the case of hemorrhagic shock. However, large volumes are often used and the fluid therapy must be continued for several days. The events occurring in the damaged microvasculature during and following burn injury cannot be classified as an example of ischemia followed by reperfusion. However, it has been proposed that the "leaky" microvasculature observed following burn in the injured tissue, and the functional impairment of distal organs (heart, lungs and liver), is in part due to oxygen radicals. Treatment with the DFO and biopolymer according to the present invention result in decreased volume demand (=less leaky microvasculature) and improved function of distal organs (=improved cardiac output, lung function and liver blood flow).

The invention is illustrated by the following examples.

EXAMPLE 1

Treatment of Burn Injury

Model

Twentythree adult sheep, weighing 40–50 kg, were studied. Sheep were prepared with chronic soft tissue lymph fistulas and vascular catheters. Vascular catheters included a swan ganz catheter, carotid arterial line, and jugular venous line. Animals were allowed to recuperate for at least 3 days after the surgical procedure.

Burn Injury

After a 2 hour anesthesia baseline period, a 40% third degree body burn was produced under halothane nitrous anesthesia. The burn involved bilateral prefemoral areas over the distribution of bilateral flanks. Resuscitation was begun immediately post burn. The animals were then monitored for 6 hours, then sacrificed. Three groups of animals were studied.

Group 1: Ringers alone as resuscitation fluid;
Group 2: 5% hydroxyethyl starch alone as resuscitation fluid:
Group 3: 5% deferoxamine chelator attached i.e. (covalently bonded) to hydroxyethyl starch alone as resuscitation fluid.

Physiologic Measurements

Aortic, central venous, pulmonary arterial, and pulmonary wedge pressures as well as cardiac output were recorded. Hourly values for arterial and venous blood gases as well as co-oximetry were measured. Co-oximetry measurements include total hemoglobin, reduced hemoglobin, oxygen content, oxygen saturation, and oxygen capacity. Dynamic and static lung compliance was also measured. Urine output and specific gravity were recorded.

Biochemical Measurements

Malondialdehyde (MDA), a measure of lipid peroxidation, was measured in both lung and liver tissue.

Results

1) Group 3, receiving iron chelator atached to hydroxyethyl starch, required significantly less fluid to maintain hemodynamic stability than either of the other two groups.

2) The lipid peroxidation level of Group 3 in both lung and liver tissue was within normal levels compared to marked increases in the other groups.

| | MDA nMol/g tissue | | |
|---|---|---|---|
| NORMAL (n = 6) | GROUP 1 RINGERS ALONE (n = 6) | GROUP 2 COLLOID ALONE (n = 2) | GROUP 3 DESFERAL COLLOID (n = 5) |
| LUNG 47 + 6 | 63 + 13 | 67 + 4 | 45 + 3 |
| LIVER 110 + 7 | 202 + 59 | 211 + 9 | 95 + 26 | n = number of sheep in group.

3) Urine hemolysis seen with burn injury was abolished in Group 3.

4) In the acute resuscitation period following burn injury (1–2 hrs), an increase in oxygen consumption was noted with the desferal colloid solution, as compared to the Ringers and colloid groups that either had a decrease or no change from controls.

These results show normal levels of lipid peroxidation and greater hemodynamic stability with less fluid volume required. Animals treated with the colloid-chelator conjugate (i.e. the DFO covalently bonded to hydroxyethyl starch) had improved perfusion and blood flow distribution as evidenced by an increase in oxygen consumption.

EXAMPLE 2

Treatment of Hemorrhagic Shock

Model

A porcine hemorrhagic shock model was used to evaluate the effects of 3 resuscitation fluids on survival and hepatic function. Fasted swine (14–16 kg) underwent spleneotomy and placement of arterial and venous catheters.

Injury

Awake animals were then bled at 1 ml/kg/min to a mean pressure of 40 mmHg, maintained for 1 hour, and resuscitated over 30 mins. with 1 of 3 fluids: LR— (n=4) at 3 ml/ml shed blood: PS/LR —5% in LR (n=5) at 1 ml/ml shed blood; DFO-PS/LR—5% PS with 7.5 mg DFO/ml (n=6) at 1 ml/ml shed blood.

Results

There were no significant differences between groups in MAP, HR, CVP, T or Hct at baseline or after resuscitation. LR treated animals all survived less than 2.5 hrs, after resuscitation, whereas PS/LR and DFO-PS/LR survived to sacrifice at 24 hours (P 0.01). AST levels (IU/L) showed no significant difference pre-op and post-resuscitation, but were elevated for PS/LR vs. DFO-SR/LR (338+/−161 vs. 106+/−57, p 0.03. Colloid resuscitation significantly prolonged survival in this hemorrhage model. This data suggests that DFO conjugate may preserve hepatocyte or microvascular integrity in hemorrhagic shock. Animals treated with the DFO-conjugate seem to have better perfusion of injured tissue, based on hermodynamic variables, than those receiving conventional fluid resuscitation with colloid alone or crystalloid.

Abbreviations used above in this example have the following meanings:
LR lactated Ringers
PS pentastarch (a form of hydroxyethyl starch)
DFO-PS DFO/PS conjugate
AST aspartate amino transferase

We claim:

1. A method of fluid resuscitation of a human or animal body in need of fluid resuscitation comprising parenterally administering to said body effective amounts of deferoxamine and a water-soluble biopolymer.

2. A method of claim 1, wherein the deferoxamine and biopolymer are covalently bonded together.

3. A method according to claim 1 or 2, wherein the biopolymer comprises a polysaccharide.

4. A method according to claim 3, wherein the deferoxamine is covalently bonded directly to one or more aldehyde groups on the polysaccharide.

5. A method according to claim 3, wherein the polysaccharide is dextran, hyaluronic acid, inulin or a starch.

6. A method according to claim 1 or 2, wherein the biopolymer comprises a protein.

7. A method according to claim 6, wherein the deferoxamine is covalently bonded directly to one or more amino, carboxyl or thiol groups on the protein.

8. A method according to claim 1, wherein the protein comprises a plasma protein fraction or hemoglobin.

9. A method according to claim 1, wherein the deferoxamine and biopolymer are formulated as an aqueous solution suitable for parenteral administration.

10. A method according to claim 1, wherein the fluid resuscitation is effected for ameliorating systemic oxidant injury occurring during ischemia and subsequent reperfusion.

11. A method according to claim 1, wherein the body has suffered burn injury.

12. A method according to claim 1, wherein the body has suffered hemorrhagic shock.

13. A method according to claim 1, wherein the deferoxamine and the biopolymer are not covalently bound or otherwise conjugated together.

14. A method according to claim 1, wherein said deferoxamine and water-soluble biopolymer are administered intravenously to said body.

* * * * *